United States Patent [19]

King

[11] Patent Number: 4,665,093
[45] Date of Patent: May 12, 1987

[54] PESTICIDAL TIN SALTS OF HYDROXAMIC ACIDS

[75] Inventor: William F. King, Novato, Calif.

[73] Assignee: Chevron Research Company, San Francisco, Calif.

[21] Appl. No.: 771,375

[22] Filed: Aug. 29, 1985

[51] Int. Cl.$^4$ .................. A01N 55/04; A61K 31/32; C07F 7/22
[52] U.S. Cl. ........................................ 514/493; 556/37
[58] Field of Search .......................... 556/37; 514/493

[56] References Cited

U.S. PATENT DOCUMENTS

| | | | |
|---|---|---|---|
| 3,170,953 | 2/1965 | Lashua | 556/37 X |
| 3,210,245 | 10/1965 | Merten et al. | 556/37 X |
| 3,275,659 | 9/1966 | Weissenberger | 556/37 X |
| 3,367,959 | 2/1968 | Fetscher et al. | 556/37 X |
| 3,520,910 | 7/1970 | Lengnick et al. | 556/37 |
| 3,629,446 | 12/1971 | Frohberger et al. | 514/493 X |
| 4,565,812 | 1/1986 | King | 514/189 |
| 4,567,284 | 1/1986 | Monzyk et al. | 556/37 |
| 4,584,317 | 4/1986 | King | 514/493 |

OTHER PUBLICATIONS

Chemical Abstracts 94 15820g (1981).
Chemical Abstracts 95 196495u (1981).

Primary Examiner—Helen M. S. Sneed
Attorney, Agent, or Firm—S. R. LaPaglia; T. G. DeJonghe; S. L. Biggs

[57] ABSTRACT

Compounds of the formula:

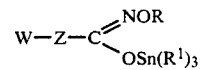

wherein W is aryl of 6 to 12 carbon atoms, substituted aryl of 6 to 12 carbon atoms substituted with 1 to 3 substituents independently selected from halogen, nitro, lower alkoxy of 1 to 3 carbon atoms, lower alkylthio of 1 to 3 carbon atoms, lower alkyl of 1 to 3 carbon atoms; lower cycloalkyl of 3 to 7 carbon atoms; or substituted lower cycloalkyl of 3 to 7 carbon atoms substituted with 1 to 3 lower alkyl groups; Z is a direct link, lower alkylene of 1 to 6 carbon atoms, or lower alkenylene of 2 to 6 carbon atoms or benzyl; R is phenyl, or lower alkyl of 1 to 6 carbon atoms; and R$^1$ is phenyl, or lower alkyl of 1 to 6 carbon atoms, lower cycloalkyl of 3 to 8 carbon atoms, either optionally substituted with 1 to 3 independently selected halogen atoms, are useful as pesticides.

29 Claims, No Drawings

PESTICIDAL TIN SALTS OF HYDROXAMIC ACIDS

BACKGROUND OF THE INVENTION

The present invention relates to organotin salts of hydroxamic acids which are fungicidal and, in same cases, insecticidal.

My commonly-assigned U.S. patent application Ser. No. 678,730 "Fungicidal Tin Salts of Heterocyclic Hydroxamic Acids" discloses fungicidal compounds of the formula:

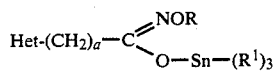

wherein Het is a 5- or 6-membered aromatic heterocyclic ring containing 1 to 2 ring nitrogen atoms and the remaining ring atoms carbon atoms optionally substituted with 1 to 2 substituents independently selected from halo, nitro, trihalomethyl, lower alkyl of 1 to 3 carbon atoms, or lower alkoxy of 1 to 3 carbon atoms; R is alkyl of 1 to 7 carbon atoms; $R^1$ is aryl of 6 to 10 carbon atoms, lower alkyl of 1 to 6 carbon atoms, cycloalkyl of 3 to 8 carbon atoms, all optionally substituted with 1 to 3 halogen atoms, and a is 0 or 1 which are fungicidal and insecticidal with the proviso that a ring nitrogen is not bonded to the hydroxamic acid

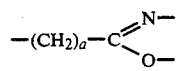

moiety.

My commonly-assigned U.S. patent application Ser. No. 676,706 now U.S. Pat. No. 4,565,812 "Fungicidal Tin Salts of Thienyl and Furyl Hydroxamic Acids" discloses compounds of the formula:

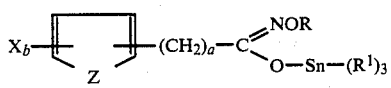

wherein Z is sulfur or oxygen; R is alkyl of 1 to 7 carbon atoms; $R^1$ is aryl of 6 to 10 carbon atoms, lower alkyl of 1 to 6 carbon atoms or cycloalkyl of 3 to 8 carbon atoms, all optionally substituted with 1 to 3 halogen atoms; a is 0 or 1; b is 0, 1, or 2; X is independently halo, nitro, trihalomethyl, lower alkyl of 1 to 3 carbon atoms which are useful as fungicides and insecticides.

My commonly-assigned U.S. Pat. No. 4,478,832 "Pesticidal O-(N-alkoxy-Substituted-Benzimidoyl) Phosphorus Esters and Thioesters" discloses insecticidal compounds of the formula:

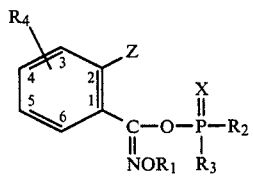

wherein X is sulfur or oxygen; $R_1$ is lower alkyl, lower alkynyl, or benzyl optionally substituted with 1 to 3 halogen atoms; $R_2$ is lower alkyl, lower alkoxy or lower alkylthio; $R_3$ is lower alkoxy, lower alkylthio, lower alkylamino or phenyl; and $R_4$ is hydrogen, cyano, trifluoromethyl, halogen, carboxyalkyl or nitro, and Z is hydrogen, cyano, trifluoromethyl, carboxyalkyl, nitro, $S(O)_n R_5$ or $SO_2 NR_6 R_7$ where n is 1 or 2, $R_5$ is lower alkyl and $R_6$ and $R_7$ are independently hydrogen or lower alkyl; provided that when $R_1$ is lower alkyl and $R_3$ is alkoxy, then $R_4$ and Z are not both hydrogen or if $R_4$ is hydrogen, Z is not nitro; and provided further that if $R_1$ is lower alkyl, $R_2$ is alkyl or alkoxy and $R_3$ is alkoxy, then $R_4$ and Z are not both hydrogen or if $R_4$ is hydrogen, Z is not nitro; and provided further that if $R_1$ is lower alkyl, $R_2$ is alkyl or alkoxy and $R_3$ is alkoxy, then if Z is hydrogen or nitro, $R_4$ is not nitro or halogen.

SUMMARY OF THE INVENTION

The present invention relates to compounds of the formula:

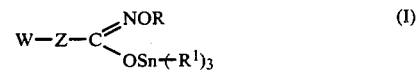

wherein W is aryl of 6 to 12 carbon atoms, substituted aryl of 6 to 12 carbon atoms substituted with 1 to 3 substituents independently selected from halogen, nitro, lower alkoxy of 1 to 3 carbon atoms, lower alkylthio of 1 to 3 carbon atoms or lower alkyl of 1 to 3 carbon atoms; lower cycloalkyl of 3 to 7 carbon atoms; or substituted lower cycloalkyl of 3 to 7 carbon atoms substituted with 1 to 3 lower alkyl groups; Z is a direct link, lower alkylene of 1 to 6 carbon atoms, or lower alkenylene of 2 to 6 carbon atoms; R is lower alkyl of 1 to 6 carbon atoms or benzyl; and $R^1$ is phenyl, or lower alkyl of 1 to 6 carbon atoms or, lower cycloalkyl of 3 to 8 carbon atoms, either optionally substituted with 1 to 3 independently selected halogen atoms; which are insecticidal and fungicidal.

Among other factors, the present invention is based upon my surprising finding that the compounds of the present invention are effective in controlling a variety of pests. In particular, these compounds are active as insecticides and, in some cases as miticides. In addition, some of the compounds of the present invention are active as fungicides. Some of these compounds also show herbicidal and/or phytotoxic activity. I have surprisingly found that the compounds where $R^1$ is cyclohexyl show surprisingly lower phytotoxicity.

Preferred W groups include phenyl, phenyl substituted with nitro, fluoro, chloro, or lower alkyl, lower alkylthio or lower alkoxy methyl; cyclopropyl or 1-methylcyclopropyl.

Especially preferred are compounds where W is 4-tolyl or phenyl.

Preferred Z groups include a direct link and vinyl.

Preferred R Groups include methyl and ethyl.

Preferred $R^1$ groups include n-butyl, cyclohexyl phenyl. Especially preferred are compounds where $R^1$ is cyclohexyl.

Definitions

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "cycloalkyl" refers to cyclic alkyl groups and refers both to those which are unsubstituted and those which are ring substituted with 1 or more alkyl groups. The term "lower cycloalkyl" refers to groups having a total of from 3 to 8 carbon atoms and includes cyclopropyl, 1-methylcyclopropyl, cyclobutyl, cyclopentyl, cyclohexyl and the like.

The term "alkylene" refers to straight- and branched-chain alkylene groups and includes, for instance, ethylene propylene, 2-methyl-propylene (e.g.

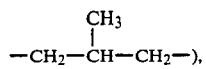

3-methyl-pentylene (e.g.,

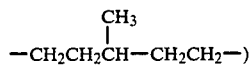

and the like. The term "lower alkylene" refers to alkylene groups having a total of 1 to 10 carbon atoms with the proviso that the chain length is no longer than 6 carbon atoms.

The term "alkylthio" refers to the group R'S— wherein R' is alkyl. The term "lower alkylthio" refers to alkylthio groups having 1 to 6 carbon atoms; examples include methylthio, ethylthio, n-hexylthio, and the like.

The term "alkoxy" refers to the group —OR' wherein R' is an alkyl group. The term "lower alkoxy" refers to alkoxy groups having from 1 to 6 carbon atoms; examples include methoxy, ethoxy, n-hexoxy, n-propoxy, isopropoxy, isobutoxy, and the like.

The term "alkenyl" refers to unsaturated alkyl groups having a double bond [e.g., $CH_3CH=CH(CH_2)_2$] and includes both straight- and branched-chain alkenyl groups. "Lower alkenyl" refers to groups having a total of from 2 to 6 carbon atoms. Typical lower alkenyl groups include, for example, vinyl, propenyl, but-3-enyl, hex-4-enyl, 2-methyl-pent-4-enyl, and the like.

The term "alkenylene" refers to straight- and branched-chain alkenylene groups [e.g., divalent aliphatic radicals which have at least one internal double bond in the chain and includes, for example, vinylene (e.g., —CH=CH—), propenylene, 3-methyl-but-2-enylene (e.g.,

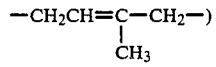

and the like.] The term "lower alkenylene" refers to alkenylene groups having a total of from 1 to 10 carbon atoms with the proviso that chain length is no longer than 6 carbon atoms.

The term "halo" or "halogen" refers to the groups fluoro, chloro, bromo and iodo.

The term "haloalkenyl" refers to alkenyl groups substituted with from 1 to 3 halogen atoms. "Lower haloalkenyl" refers to groups having a total of 2 to 6 carbon atoms, and includes, for example, 1-chloropropenyl, 2,3-dibromo-but-3-enyl, and the like.

The term "alkynyl" refers to unsaturated alkyl groups having a triple bond (e.g., $CH_3C\equiv CCH_2CH_2$) and includes both straight- and branched-chain alkynyl groups. "Lower alkynyl" refers to groups having a total of from 2 to 6 carbon atoms. Typical lower alkynyl groups include propynyl, but-3-ynyl, hex-4-ynyl, 2-methyl-pent-4-ynyl, and the like.

The term "hydroxy alkyl" refers to the group —R'-'OH wherein R'' is branched or unbranched alkylene and the hydroxy can be on a primary, secondary or a tertiary carbon. Examples include hydroxyethyl and 2-hydroxy-propyl and 2-hydroxy-2-methylbutyl.

The term "aryl" refers to aryl groups having from 6 to 12 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of 1 to 4 carbons substituted with an aryl group of from 6 to 12 carbons and includes, for example, benzyl, p-chlorobenzyl, p-methylbenzyl and 2-phenylethyl.

The term "alkylamino" refers to the group R'R''N— wherein R' is alkyl and R'' is hydrogen or alkyl. The term "lower alkylamino" refers to alkylamino groups having 1 to 6 carbon atoms. Typical alkylamino groups include methylamino, ethylamino, diethylamino, dimethylamino, and the like.

Pests are any insect, rodent, nematode, fungus, weed, or any form of terrestrial or aquatic plant or animal life or virus, bacterial organism or other microorganism (except those viruses, bacteria or other microorganisms existing in living humans or other living animals) considered injurious to health, the environment or man's economic well-being.

DETAILED DESCRIPTION OF THE INVENTION

The compounds of the present invention are conveniently prepared according to the following reaction scheme:

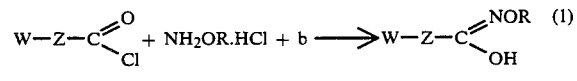

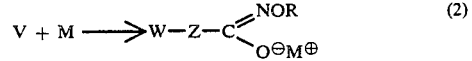

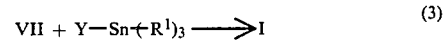

wherein W, Z, R and $R^1$ are as previously defined in conjunction with Formula I, b is a base, M is a basically reacting metal compound which is capable of removing the proton from the hydroxyl of V and Y is halogen.

Reaction (1) is conducted by combining II, III, and IV in solvent. It is preferred to add II in solvent to a precooled mixture (to about 0° C. to about −5° C.) of III and IV in water/organic solvent, maintaining the cooling during the addition. Suitable organic solvents include methylene chloride, chloroform, ether, toluene, and the like. Certain acid chlorides, II, are commercially available, others may be conveniently prepared from the corresponding carboxylic acid by conventional procedures. Suitable bases, $b_1$, include inorganic bases such as potassium carbonate, sodium carbonate, sodium hydroxide, and the like. It is preferred to add an excess of III and IV relative to II, on the order of about 1.10 to about 1.25 equivalents III per equivalent II and about 1.15 to about 1.30 equivalents IV per equivalent II. The reaction is conducted at a temperature of about $-15°$ C. to about $10°$ C., preferably from about $-5°$ C. to about $0°$ C., and is generally complete within about 4 to about 16 hours. The product, V, is isolated by conventional procedures such as extraction, filtration, washing, stripping, and the like.

Reaction (2) is conducted by combining approximately equimolar amounts of V and VI in solvent. It may be preferred to add a slight excess of VI relative to V, on the order of about 1.02 to about 1.05 equivalents VI per equivalent V. It is preferred to add VI to V in solvent. Suitable basically reacting metal compounds, M, include alkali (Group IA) metals such as sodium and potassium, also sodium hydride, butyllithium, and the like. Suitable solvents include low molecular weight alcohols such as methanol and ethanol, also dimethoxy ethane, tetrahydrofuran, ether, and the like. The reaction is conducted at a temperature of from about $0°$ C. to about reflux, preferably from about $0°$ C. to about $20°$ C. or for convenience at ambient temperature, and is generally complete within about 0.5 to about 1.5 hours. The product, VII, is isolated by conventional procedures such as stripping and the like. Alternatively, after stripping and chasing of the solvent, product VII may be used directly in Reaction (3) without further isolation.

Reaction (3) is conducted by combining approximately equimolar amounts of VII and VIII in solvent. It is preferred to add VIII to VII in solvent, in order to obtain improved yields. Suitable solvents include organic solvents such as dimethoxyethane, tetrahydrofuran, low molecular weight dialkyl ethers, and the like. The reaction is conducted at a temperature of from about $0°$ C. to about $35°$ C., preferably from about $5°$ C. to about $35°$ C. or at reflux, and is generally complete within about 6 to about 10 hours. The product, I, is isolated by conventional procedures such as stripping, extraction, washing, filtration, and the like.

Utility

The compositions and methods of the present invention are useful in controlling a variety of pests, including insects, acarines, certain plant fungal infections and undesired vegetation.

These compounds are active as fungicides and are particularly effective in controlling a variety of fungi which are deleterious to plants, including plant fungal infections. These compounds are particularly effective in controlling leaf spot diseases. Some of these compounds are particularly useful in controlling fungal organisms such as *Aspergillus niger, Piricularia oryzae, Phytophthora infestans, Erysiphe polygoni* and *Fusarium moniloforne*.

These compounds are also effective as insecticides and acaricides and may be used in controlling a variety of insect and arthropod pests. In particular, some of these compounds are particularly effective in controlling acarines such as mites and lepidopteraus such as cabbage loopers.

Like most insecticides and acaricides, the compounds are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hostages susceptible to insect attack. It may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from about 5% to 80% insecticide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the insecticidal composition.

Dusts are freely flowing admixtures of the active insecticide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the insecticide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for insecticidal applications include simple solutions of the active insecticide in a dispersant in which it is completely soluble at the desired concentration, such as acetone, alkylated naphthalenes, xylene, or other organic solvents. Granular formulations, wherein the insecticide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying insecticides are well known in the art.

The percentages by weight of the insecticide may vary according to the manner in which the composition is to be applied and the particular type of formulation, but in general comprise 0.5% to 95% of the toxicant by weight of the insecticidal composition.

The insecticidal compositions may be formulated and applied with other active ingredients, including nematocides, insecticides, fungicides, bactericides, plantgrowth regulators, fertilizers, etc. In applying the chemical, an effective amount and concentration of the toxicant of this invention is, of course, employed.

When used as a fungicide, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicide of this invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A particularly preferred embodiment for the herbicidal compositions is as a wettable powder. The wettable powder desirably contains the above-mentioned herbicidally-active compound and an inert carrier such as kaolin clay, talc, atapulgite, calcium carbonate or magnesium carbonate. Kaolin clay is an especially preferred inert carrier. Also, desirably the composition contains a surfactant or dispersing agent such as are known in the art for aiding the dispersion of the finely-divided powder ingredients of the composition in a solvent such as water. The surfactant may be of the nonionic type or the ionic type and can be selected from materials such as calcium alkyl sulfonates or sodium lauryl sulfonate, or a lignosulfonate salt.

Preferred amounts of the ingredients of the composition are 1–90% active compound, 10–95% inert carrier and 0.5–15% surfactant. More preferred ranges are 10–80% active, 20–90% inert carrier and 1–9% surfactant. Particularly preferred wettable powder herbicidal compositions of the present invention contain about 40–60% active, 40–60% inert carrier and 2–8% surfactant. Percentages in this specification are by weight unless indicated otherwise.

The herbicidal composition of the present invention may alternatively be formulated as a "flowable" with either an oil or water base. In the instance of a flowable herbicidal composition, the oil or water base is considered, for purposes of the present specification, as the inert carrier. Desirably, the flowable composition will also contain a suspending agent or thickener. Types of suspending agents known in the art include the following: density suspension, clay suspension, polymer suspension or surfactant suspension.

Preferably, the flowable herbicidal composition in accordance with the present invention contains 20–70% active, 30–80% inert carrier (oil or water base), and 1–10% suspending agent.

In the case of either the wettable powder or the flowable herbicidal composition of the present invention, preferably the active compound is micronized; that is, very finely divided into particle sizes between about 0.5 and 20 microns, more preferably between 2 and 8 microns, for purposes of formulating the final herbicidal composition.

Preferred amounts of the fungicidal, insecticidal and acaricidal compositions are from about 0.5 to about 95% by weight active compound (ingredient), from about 5 to about 99.5% inert carrier and about 0 to about 20% of a surfactant.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of N-Methoxy-benzhydroxamic Acid

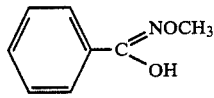

To a stirred mixture of 0.312 mole methoxyamine hydrochloride in cooled (to about 0° C.) water, 0.312 mole potassium carbonate was added in portions; the temperature of the reaction mixture was maintained at about 0° C. during the addition. To that cool mixture, 0.25 mole benzoyl chloride dissolved in methylene chloride (about 300 ml) was added dropwise over about 0.5 hours. The temperature of the reaction mixture was kept at about 0 to 10° C. for the first hour; the reaction mixture was then allowed to come to room temperature and was stirred overnight. The layers were phase separated. The methylene chloride layer was dried over magnesium sulfate and then stripped. The residue was washed with cold ethyl ether/hexane to give the above-identified product as an off-white solid, melting point 58–60° C.

EXAMPLE 2

Preparation of Tri-n-butylstannyl-O-(N-methoxy-benzyl Carboximidoate)

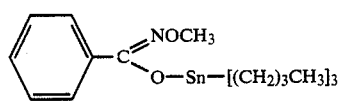

(a) To a stirred mixture of 5.3 g (0.0351 moles) N-methoxy-benzhydroxamic acid in about 100 ml 50/50 dimethoxy ethane/methanol, 0.8 g (0.036 moles) sodium metal were added slowly. When the sodium metal had dissolved, the dimethoxy ethane/methanol was removed by stripping under reduced pressure and heat to give the corresponding sodium salt.

(b) Dimethoxy ethane (about 75 ml) was added to the sodium salt from Step (a). To the resulting solution, 9.3 g (0.030 moles) tri-n-butyl tin fluoride was added. The reaction mixture was refluxed about 16 hours. The dimethoxy ethane was removed by stripping. Water (about 75 ml) and methylene chloride (about 125 ml) were added to the residue and the resulting mixture was stirred. The layers were phase separated. The methylene chloride layer was washed once with water, dried over magnesium sulfate and stripped to give the crude product. The crude product was stirred with charcoal, celite and magnesium sulfate for about one hour; then filtered and stripped to give about 6.8 g of the above-identified product, as a colorless liquid.

Elemental analysis for $C_{20}H_{35}NO_2Sn$ showed: Calculated %C 54.6, %H 8.01, and %N 3.18; found % C55-88; %H 7.69, and %N 3.72.

EXAMPLE 3

Preparation of Trimethylstannyl-O-(N-methoxy-benzyl Carboximidoate)

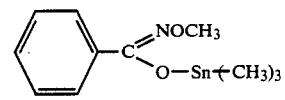

(a) To a stirred mixture of 5 g (0.0331 moles) N-methoxy-benzhydroxamic acid (the product of Example 1 in about 50 ml methanol, 0.8 g (0.034 moles) sodium metal was added very slowly, allowing hydrogen gas to evolve. Removal of methanol by reduced pressure and heat gave the corresponding sodium salt which was used in Step (b) without further isolation.

(b) Fresh methanol (about 25 ml) was added to the salt from Step (a). To the resulting stirred mixture, 6.8 g (0.034 moles) trimethyl tin chloride was added in one portion. The reaction mixture was refluxed overnight, for a day and then was warmed (to 40° C.) overnight. The methanol was removed by reduced pressure and heat. Water (about 50 ml) and methylene chloride (about 125 ml) were added to the residue and the resulting mixture was stirred. The layers were phase separated; the methylene chloride layer was washed with water, dried over magnesium sulfate, filtered and stripped to give the crude product. The crude product was stirred with charcoal and celite, then filtered and stripped to give the above-identified product, as a light amber liquid.

Elemental analysis for $C_{11}H_{17}NO_2Sn$ showed: Calculated %C 421, %H 5.46 and %N 4.46; found %C 47.79, %H 5.95, and %N 5.09.

EXAMPLE 4

Preparation of N-methoxy-2-fluorobenzhydroxamic Acid

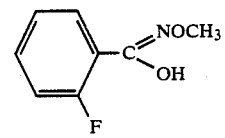

To a stirred mixture of 30.3 g (0.363 moles) methoxyamine hydrochloride and 51 g (0.37 moles) potassium carbonate in about 300 ml water/methylene chloride maintained at a temperature below −5° C., 50 g (0.32 moles) 2-fluoro-benzoylchloride were dropped in. The reaction mixture was then allowed to stir at room temperature overnight. The aqueous and methylene chloride layers were separated. The methylene chloride layer was dried over magnesium sulfate, filtered and stripped to give about 45 g of the above-identified product, as a clear amber liquid.

Elemental analysis for $C_8H_8FNO_2$ showed: calculated %C 56.8, %H 4.77, and %N 8.28; found %C 57.54, %H 5.37, and %N 8.69.

EXAMPLE 5

Preparation of Tri-n-butylstannyl-O-(N-methoxy-2-fluorobenzyl Carboximidoate)

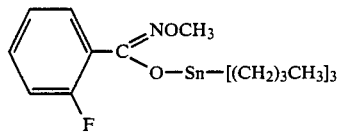

(a) To a stirred mixture of 2.54 g (0.015 moles) N-methoxy-2-fluorobenzhydroxamic acid in methanol (about 50 ml), 0.4 g (0.017 moles) sodium metal was added slowly. The mixture was stirred until all the sodium had dissolved. The methanol was removed by reduced pressure and heat to give the corresponding sodium salt which was used in Step (b) without further isolation.

(b) To the sodium salt from Step (a), dimethoxy ethane (about 100 ml) was added. The resulting mixture was stirred while 4.8 g (0.015 moles) tributyl tin chloride was added dropwise. The reaction mixture was refluxed 8 hours and then stirred overnight at room temperature. The dimethoxyethane was removed by stripping; methylene chloride (about 125 ml) and water (about 50 ml) were added to the residue and the resulting mixture was stirred. The layers were phase separated after each water wash. The methylene chloride layer was washed two more times with water, dried over magnesium sulfate, and filtered. The methylene chloride was stripped to give about 5.6 g of the above-identified product, as a liquid.

Elemental analysis for $C_{20}H_{34}FNO_2Sn$ showed: Calculated %C 52.4, %H 7.48, and %N 3.06; found %C 51.48, %H 8.02, and %N 2.3.

EXAMPLE 6

Preparation of N-Methoxy-4-methyl-cinnamylhydroxamic Acid

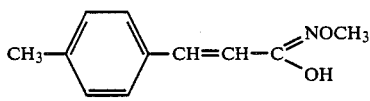

(a) To a stirred mixture of 100 g (0.62 moles) p-methylcinnamic acid in methylene chloride (about 30 ml), 88 g (0.74 moles) thionyl chloride was added dropwise. The reaction mixture was then refluxed for 24 hours. The methylene chloride was removed under reduced pressure and heat to give the corresponding p-methylcinnamic acid chloride. Fresh methylene chloride was added to the acid chloride; half of which was used in Step (b).

(b) To an aqueous solution of 51.4 g (0.37 moles) potassium carbonate and 31.1 g (0.372 moles) methoxyamine (in about 300 ml), one-half of the acid chloride from Step (a) (about 0.3 moles) in methylene chloride (about 300 ml) was added dropwise. The reaction mixture was stirred for about 4 hours. The layers were phase separated. The methylene chloride layer was dried, removed, washed with water and dried over magnesium sulfate to give about 55 g of the above-identified product as a solid.

Elemental analysis for $C_{11}H_{13}NO_2$ showed: calculated %C 69.1, %H 6.85, and %N 7.33; found %C 69.3, %H 6.9, and %N 7.0.

EXAMPLE 7

Preparation of Tricyclohexylstannyl-O-(N-Methoxy-4-methylcinnamyl Carboximidoate)

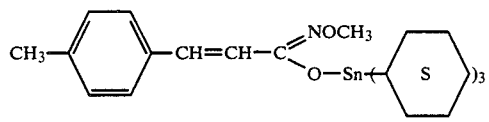

(a) A mixture of 2.9 g (0.015 moles) N-methoxy-4-methyl-cinnamylhydroxamic acid (the product of Example 6), and 1 g (0.0178 moles) potassium hydroxide in about 50 ml ethanol was stirred and warmed for about one hour. To that mixture, 6.7 g (0.015 moles) tricyclohexyl tin bromide were added. The reaction mixture was refluxed 8 hours. The ethanol was removed by reduced pressure and heat. Water (about 50 ml) and methylene chloride (about 100 ml) were added to the residue and the resulting mixture was stirred. The layers were phase separated. The methylene chloride layer was washed 3 times with water. The methylene chloride layer was dried over magnesium sulfate, filtered and stripped. The residue was washed with methylene chloride, treated with charcoal and celite, then filtered and stripped to give about 7 g of the above-identified product, as a thick liquid.

Elemental analysis for $C_{29}H_{45}NO_2Sn$ showed: Calculated %C 62.8, %H 8.12, and %N 2.51; found %C 62.37, %H 9.86, and %N 2.14.

EXAMPLE 8

Preparation of N-methoxy-2-trifluoromethylbenzhydroxamic Acid

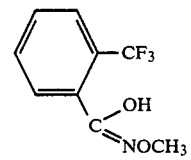

To a stirred solution of 25 g (0.30 mole) methoxyamine hydrochloride ($NH_2OCH_3 \cdot HCl$) and 43 g (0.31 moles) potassium carbonate in about 200 ml ice water, 50 g (0.259 moles) of 2-trifluoromethyl-benzoylchloride were added at a slow to moderate dropping rate. The reaction mixture was stirred overnight. The mixture was suction-filtered and the residue, the crude product, was dried in a vacuum oven. The crude product was then washed with hexane (about 100 ml) and diethylether (about 2 to 3 ml), as an extra purifying step, to give the product a white solid, melting point 101° to 103° C.

Elemental analysis for C9H8F3NO2 showed: Calculated %C 49.3, %H 4.14, and %N 6.39; found %C 49.56, %H 3.68, and %N 6.49.

EXAMPLE 9

Preparation of N-methoxy-4-cyanobenzhydroxamic acid

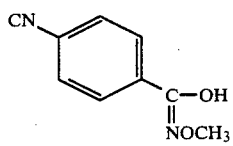

A mixture of 29.4 g (0.350 moles) methoxyaminehydrochloride and 50 g (0.36 moles) potassium carbonate in about 200 ml ice water was stirred, maintaining the temperature below -5° C. until the reactants were dissolved. To that solution, 50 g (0.302 moles) 4-cyanobenzoylchloride were dropped in slowly, maintaining the temperature of the reaction mixture below 0° C. during the addition. The reaction mixture was stirred overnight. The reaction mixture was suction-filtered. The residue, containing the crude product was dried in a heated vacuum oven and then washed with hexane (about 100 ml) and ether (about 2-3 ml) to give the product an off-white solid.

Elemental analysis for C9H8N2O2 showed: Calculated %C 61.4, %H 4.58, and %N 15.9; found %C 55.4, %H 3.78, and %N 14.1.

EXAMPLE 10

Preparation of N-methoxycyclopropylhydroxamic Acid

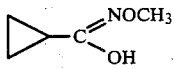

To a mixture of 69.1 g (0.5 moles) potassium carbonate in about 100 ml water, 41.8 g (0.5 moles) of methoxyamine hydrochloride (H2NOCH3:HCl) in about 20 ml water was added and the resulting mixture stirred about 20 minutes, maintaining its temperature in the range of about 0° to about 10° C. with an ice bath. To that mixture, 47 g (0.45 moles)

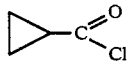

(cyclopropanecarboxylic acid chloride) was added dropwise, maintaining a reaction temperature in the range of about 0° to about 10° C. The reaction mixture was allowed to stir overnight at room temperature. The crude product was obtained from the reaction mixture by filtering. The precipitate was stirred in hexane with a small amount of diethyl ether and filtered to obtain the product, an offwhite solid.

Elemental analysis for C5H9NO2 showed: Calculated %C 52.5, %H 7.88, and %N 12.2; found %C 53.6, %H 8.71, and %N 12.2.

EXAMPLE 11

Preparation of N-methoxy-2-(p-chlorophenyl)-3-methylbutylhydroxamic Acid

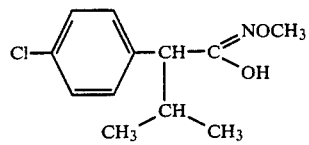

(a) A mixture 50 g (0.28 moles) of 2-(p-chlorophenyl)-3-methylbutyric acid,

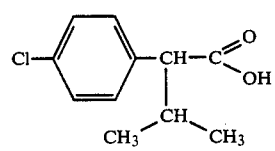

in about 300 ml methylene chloride with a catalytic amount (about 1 ml) pyridine was stirred at room temperature for about one-half hour. To that mixture 39 g (0.33 moles) thionyl chloride in abut 20 ml methylene chloride was added dropwise. After the addition was complete, the reaction mixture was refluxed for about 16 hours. The methylene chloride was then removed under reduced pressure and heat. Water (about 100 ml) and fresh methylene chloride (about 200 ml) was added to the residue, the resulting mixture was stirred. The phases were separated, the methylene chloride (organic) phase extracting the product, the acid chloride. The methylene chloride layer was dried over magnesium sulfate and filtered. Stripping of the methylene chloride gave the corresponding acid chloride which was used in the second step of the reaction without further isolation.

(b) To stirred mixture of 28 g (0.33 moles) of methoxyamine hydrochloride and 17 g (0.34 moles) potassium carbonate in about 150 ml water whose temperature was maintained below 0° C., 65 g (0.28 moles) of the acid chloride of step (a) in about 150 ml methylene chloride was added dropwise. The temperature of the reaction mixture was maintained below 0° C. during the addition. After the addition was complete, the reaction mixture was stirred at room temperature for about 4 hours. The phases were separated, the methylene chloride layer extracting the product. The methylene chloride layer was dried over magnesium sulfate and filtered. Stripping of the methylene chloride gave the product, an amber viscous liquid which solidified upon standing to a light yellow solid.

EXAMPLE 12

Preparation of
Tri-n-butylstannyl-O-(N-methoxy-2-nitrobenzyl Carboximidoate)

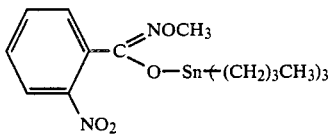

To a mixture of 3 g (0.0153 moles) N-methoxy-2-nitrobenzhydroxamic acid and 2.7 g (0.02 moles) potassium carbonate in methyl ethylketone which had been stirred and heated for one hour, 5 g (0.0154 mole) 97% tri-n-butyl tin chloride was added in one portion. The reaction mixture was refluxed 16 hours. The methylethyl ketone was removed by reduced pressure and heat. Water and methylene chloride were added to the residue; the resulting mixture was stirred one-half hour. The layers were phase separated. The methylene chloride layer was washed 3 times with water, dried with magnesium sulfate and stripped. The residue (crude product) was dissolved in hexane; the resulting solution was stirred with charcoal and then filtered. The hexane was removed by stripping to give 5.4 g of the above-identified product as a yellow liquid.

Elemental analysis for $C_{20}H_{34}N_2O_4Sn$ showed: Calculated %C 49.5, %H 7.06, and %N 5.77; found %C 49.8, %H 7.71, and %N 4.41.

EXAMPLE 13

Preparation of
Tri-n-butylstannyl-O-(N-ethoxy-2-nitrobenzyl Carboximidoate)

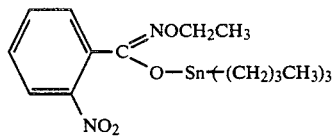

To a stirred mixture of 3 g (0.0143 moles) N-ethoxy-2-nitrobenzhydroxamic acid and 5 g (0.0138 moles) tri-n-butyl tin bromide in methylene chloride, 1.5 g (0.0148 moles) triethylamine in a small amount of methylene chloride was dropped in slowly. The reaction mixture was refluxed overnight. The heat was removed and the reaction mixture was allowed to cool. Water was added to the reaction mixture; the resulting mixture was stirred for a few minutes and the layers were phase separated. The methylene chloride layer was washed 3 times with water, dried with magnesium sulfate, filtered and stripped. The residue (crude product) washed with hexane, filtered and stripped to give the above-identified product, as a yellow green liquid.

Elemental analysis for $C_{21}H_{30}N_2O_4Sn$ showed: calculated %C 50.5, %H 7.27, and %N 5.61; found %C 49.73, %H 7.35, and %N 5.36.

EXAMPLE 14

Preparation of
N-methoxy-1-methyl-cyclopropylhydroxamic Acid

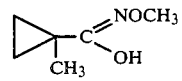

To a solution of 41 g (0.49 moles) methoxyamine hydrochloride and 70 g (0.51 moles) potassium carbonate in a small amount of iced water (about 100 ml), 50 g (0.422 moles) 1-methylcyclopropane carboxylic acid chloride was added dropwise, maintaining the temperature of the reaction mixture at -10° C. during the addition. After the addition was complete, methylene chloride (about 400 ml) was added to the reaction mixture and the resulting mixture was stirred overnight at room temperature. The layers were phase separated. The methylene chloride layer was dried over magnesium sulfate, filtered and stripped. The residue was washed with hexane and water, suction filtered and dried in a vacuum oven to give about 30 g of the above-identified product, as an off-white solid.

Elemental analysis for $C_6H_{11}NO_2$ showed: Calculated %C 55.8, %H 8.59, and %N 10.9; found %C 53.8, %H 8.29, and %N 9.91.

EXAMPLE 15

Preparation of
Tri-n-butylstannyl-O-(N-methoxy-1-methylcyclopropylcarboximidoate

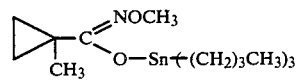

A stirred mixture of 2 g (0.0155 moles) N-methoxy-1-methyl-cyclopropylhydroxamic acid (the product of Example 14) and 2.7 g (0.02 moles) potassium carbonate in methylethyl ketone (about 75 ml) was heated about one hour. To that mixture, 5 g (0.0154 moles) tributyl tin chloride was added in one portion. The reaction mixture was refluxed about 16 hours. The methylethylketone was removed by reduced pressure and heat. Water (about 50 ml) and methylene chloride (about 125 ml) were added to the residue and the resulting mixture was stirred for about 15 minutes. The layers were phase separated. The methylene chloride fraction was washed 3 times with water, dried with magnesium sulfate, filtered and stripped to give the crude product. The crude product was dissolved in hexane, stirred (treated) with charcoal for about an hour and filtered. Stripping of the hexane gave about 4 g of the above-identified product as a clear, colorless liquid.

Elemental analysis for $C_{18}H_{37}NO_2Sn$ showed: Calculated %C 51.7, %H 8.92, and %N 3.35; found %C 52.38, %H 9.3, and %N 1.66.

Compounds made in accordance with the methods disclosed in the Detailed Description of the Invention and in Examples 1 to 15, using the appropriate starting materials and reagents are disclosed in Table I.

In addition, by following the methods disclosed in the Detailed Description of the Invention and in Examples 1 to 15 and using the appropriate starting materials and reagents, the following compounds are made:

triphenylstannyl-O-(N-methoxy-2-trifluoromethylbenzyl carboximidoate);
tricyclohexylstannyl-O-(N-ethoxy-2-trifluoromethylbenzyl carboximidoate);
tri-n-butylstannyl-O-(N-methoxy-4-cyano-benzyl carboximidoate);
tricyclohexylstannyl-O-N-methoxy-4-cyanobenzyl carboximidoate);
tri-n-butylstannyl-O-N-methoxy-cyclopropyl carboximidoate);
tri-n-butylstannyl-O-N-methoxy-4-methyl-cinnamyl carboximidoate);
triphenylstannyl-O-N-methoxy-4-methyl-cinnamyl carboximidoate);
tricyclohexylstannyl-O-N-ethoxy-4-methyl-cinnamyl carboximidoate);
tricyclohexylstannyl-O-N-benzyl-4-methyl-cinnamyl carboximidoate); and
tricyclohexylstannyl-O-N-methoxy-cinnamyl carboximidoate).

EXAMPLE A

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium moniloforme, Botrytis cinerea, Aspergillus niger* and *Ustilago hordeii*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of mg/cm$^2$ needed for 99% control of the fungus (ED$_{99}$). The effectiveness of the compounds for fungicidal activity are reported in Table II in terms of the percent of the ED$_{99}$ of the test compound of the ED$_{99}$ of the standard Difolatan ®.

EXAMPLE B

Tomato Late Blight

Compounds were tested for the preventative control of the Tomato Late Blight organism *Phytophthora infestans*. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE C

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

EXAMPLE D

Tomato Early Blight

Compounds were tested for the control of the Tomato Early Blight organism *Alternaria solani*. Tomato (variety Bonny Best) seedlings of 6- to 7-weeks old were used. The tomato plants were sprayed with a 200-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table II.

EXAMPLE E

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table II.

EXAMPLE F

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table II.

EXAMPLE G

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66°-68° F. and 60-80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table II.

EXAMPLE H

Aphid Control

The compounds of this invention were tested for their insecticidal activity against cotton aphids (*Aphis gossypii* Glover). An acetone solution of the test compound containing a small amount of nonionic emulsifier was diluted with water to give a concentration of 40 ppm. Cucumber leaves infested with cotton aphids were dipped in the test compound solution. Mortality readings were taken after 24 hours. The results are tabulated in Table III in terms of percent control.

EXAMPLE I

Aphid Systemic Evaluation

This procedure is used to assess the ability of a candidate insecticide to be absorbed through the plant root system and translocate to the foliage and thus to show insecticidal activity against the cotton aphid (*Aphis gossypii* Glover).

Two cucumber plants planted in a 4-inch fiber pot with a soil surface area of 80 cm$^2$ are used. Forty ml of an 80-ppm solution of the candidate insecticide is poured around the plants in each pot. (This corresponds to 40 gamma/cm$^2$ of actual toxicant.) The plants are maintained throughout in a greenhouse at 75°-85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table III in terms of percent control.

EXAMPLE J

Mite Adult

Compounds of this invention were tested for their insecticidal activity against parathion-resistant Two-spotted Spider Mite (*Tetranychus urticae* Koch). An acetone solution of the candidate toxicant containing a small amount of nonionic emulsifier was diluted with water to 40 ppm. Lima bean leaves which were infested with mites were dipped in the toxicant solution. The results are tabulated in Table III in terms of percent control.

EXAMPLE K

Mite Egg Control

Compounds of this invention were tested for their ovicidal activity against eggs of the two-spotted spider mite (*Tetranychus urticae* Koch). An acetone solution of the test toxicant containing a small amount of nonionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° C. to 33° C. for seven days. On the eighth day egg mortality readings are taken. The results, expressed as percent control, are tabulated in Table III.

EXAMPLE L

Housefly

Compounds of this invention were tested for their insecticidal activity against the Housefly (*Musca domestica* Linnaeus). A 500-ppm acetone solution of the candidate toxicant was placed in a micro sprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table III in terms of percent control.

EXAMPLE M

American Cockroach

Compounds of this invention were tested for their insecticidal activity against Chlordane-resistant American Cockroaches (*Periplaneta americana* Linnaeus). A 500-ppm acetone solution of the candidate toxicant was placed in a micro sprayer (atomizer). A random mixture of anesthetized male and female roaches was placed in a container and 55 mg of the above-described solution was sprayed on them. A lid was placed on the container. A mortality reading was made after 24 hours. The results are tabulated in Table III in terms of percent control.

EXAMPLE N

Alfalfa Weevil

The compounds of this invention were tested for their insecticidal activity against Alfalfa Weevil [*Hypera brunneipennis* (Boheman)]. A 500-ppm acetone solution of the candidate toxicant was placed in a micro sprayer (atomizer). A random mixture of male and female weevils was placed in a container and 55 mg of the above-described acetone solution was sprayed on them. A lid was placed on the container. A mortality reading was made after 24 hours. The results are tabulated in Table III in terms of percent control.

EXAMPLE O

Cabbage Looper Control

The compounds of this invention were tested for their insecticidal activity against Cabbage Looper [*Trichoplusia ni* (Hubner)]. An acetone solution of the candidate toxicant containing a small amount of nonionic emulsifier was diluted with water to give a concentration of 500 ppm. Excised cucumber leaves were dipped in the toxicant solution and allowed to dry. The leaves were then infested with Cabbage Looper larvae. Mortality readings were taken after 24 hours. The results are tabulated in Table III in terms of percent control.

EXAMPLES P AND Q

The compound was respectively tested for pre-emergent and post-emergent activity against a variety of grasses and broad-leaf plants including one grain crop and one broad-leaf crop.

EXAMPLE P

Pre-Emergent Herbicide Test

Pre-emergence herbicidal activity was determined in the following manner.

An acetone solution of the test compound was prepared by mixing 750 mg of the test compound, 220 mg of a nonionic surfactant and 25 ml of acetone. This solution was added to approximately 125 ml of water containing 156 mg of surfactant.

Seeds of the test vegetation were planted in a pot of soil and the test compound solution was sprayed uniformly onto the soil surface at a dose of 27.5 micrograms/$cm^2$. The pot was watered and placed in a greenhouse. The pot was watered intermittently and was observed for seedling emergence, health of the emerging seedlings, etc., for a 3-week period. At the end of this period the herbicidal effectiveness of the test compound was rated based on the physiological observations. A 0-to-100-scale was used, 0 representing no phytotoxicity and 100 representing complete kill. The results of these tests are summarized in Table IV, hereinbelow.

EXAMPLE Q

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 27.5 micrograms/$cm^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100-scale was used, 0 representing no phytotoxicity and 100 representing complete kill. The results of these tests are summarized in Table IV.

TABLE I

Compounds of the formula:

$$W-Z-C(=NOR)-OSn-(R^1)_3$$

| Compound No. | W | Z | R | $R^1$ | Physical State | %C Calc. | %C Fd. | %H Calc. | %H Fd. | %N Calc. | %N Fd. | %Cl Calc. | %Cl Fd. |
|---|---|---|---|---|---|---|---|---|---|---|---|---|---|
| 1  42642 | phenyl | — | —CH$_3$ | —CH$_3$ | light amber liquid | 42.1 | 47.8 | 5.46 | 5.95 | 4.46 | 5.09 | | |
| 2  42533 | phenyl | — | —CH$_3$ | —(CH$_2$)$_3$CH$_3$ | colorless liquid | 54.6 | 55.9 | 8.0 | 7.69 | 3.18 | 3.72 | | |
| 3  43531 | phenyl | — | —CH$_3$ | cyclohexyl-S | opaque liquid, mp 71–75° | 60.3 | 59.0 | 7.97 | 8.26 | 2.70 | 1.92 | | |
| 4  45266 | 2-NO$_2$-phenyl | — | —CH$_3$ | —(CH$_2$)$_3$CH$_3$ | yellow liquid | 49.5 | 49.8 | 7.06 | 7.71 | 5.77 | 4.41 | | |
| 5  45129 | 2-NO$_2$-phenyl | — | —CH$_2$CH$_3$ | —(CH$_2$)$_3$CH$_3$ | yellow green liquid | 50.5 | 49.7 | 7.27 | 7.35 | 5.61 | 5.36 | | |
| 6  45058 | 2-NO$_2$-phenyl | — | —CH$_2$CH$_3$ | cyclohexyl-S | light green solid, mp 57–61° C. | 56.2 | 59.0 | 7.33 | 7.96 | 4.85 | 3.41 | | |

TABLE I-continued

Compounds of the formula:
$$W-Z-C(=NOR)-OSn-(R^1)_3$$

| Compound No. | W | Z | R | R¹ | Physical State | % C Calc. | % C Fd. | % H Calc. | % H Fd. | % N Calc. | % N Fd. | % Cl Calc. | % Cl Fd. |
|---|---|---|---|---|---|---|---|---|---|---|---|---|---|
| 7 44876 | o-NO₂-phenyl | — | —CH₂-phenyl | thiacyclohexyl | pale yellow solid, mp 86–107° C. | 51.3 | 53.9 | 6.46 | 7.99 | 6.91 | 3.99 | | |
| 8 44104 | 2-methyl-4-NO₂-phenyl (2,4-dinitro) | — | —CH₃ | thiacyclohexyl | tan solid, mp 148–153° C. | 51.3 | 53.9 | 6.46 | 7.99 | 6.91 | 3.99 | | |
| 9 44570 | o-F-tolyl | — | —CH₃ | —(CH₂)₃CH₃ | yellow liquid | 52.4 | 51.5 | 7.48 | 8.02 | 3.06 | 2.3 | | |
| 10 45265 | o-F-tolyl | — | —CH₃ | thiacyclohexyl | opaque semi-solid | 58.2 | 57.5 | 7.52 | 8.02 | 2.61 | 1.26 | | |
| 11 45359 | o-CF₃-tolyl | — | —CH₃ | thiacyclohexyl | opaque oil | 55.3 | 55.4 | 6.88 | 7.83 | 2.39 | 2.37 | | |
| 12 43777 | p-Cl-tolyl | —CH(HC(CH₃)₂)— | —CH₃ | thiacyclohexyl | yellow liquid | 59.2 | 59.3 | 7.95 | 8.25 | 2.30 | 2.15 | | |

TABLE I-continued

Compounds of the formula:

$$W-Z-C(=NOR)-OSn-(R^1)_3$$

| Compound No. | W | Z | R | R¹ | Physical State | %C Calc. | %C Fd. | %H Calc. | %H Fd. | %N Calc. | %N Fd. | %Cl Calc. | %Cl Fd. |
|---|---|---|---|---|---|---|---|---|---|---|---|---|---|
| 13  44828 | 4-Cl-C₆H₄ | H, —C—HC(CH₃)₂ | —CH₃ | —CH₂—C₆H₅ | opaque viscous liquid | 62.6 | 62.8 | 5.73 | 6.21 | 2.21 | 2.41 | 5.60 | 6.57 |
| 14  43778 | 4-CH₃-C₆H₄ | —CH=CH— | —CH₃ | tetrahydrothiopyranyl | yellowish liquid | 62.8 | 62.4 | 8.12 | 9.86 | 2.51 | 2.14 | | |
| 15  45287 | 1-methylcyclopropyl | — | —CH₃ | —(CH₂)₃CH₃ | clear colorless liquid | 51.7 | 52.4 | 8.92 | 9.3 | 3.35 | 1.66 | | |
| 16  45361 | 1-methylcyclopropyl | — | —CH₃ | tetrahydrothiopyranyl | white solid | 58.1 | 61.4 | 8.73 | 10.3 | 2.82 | 2.02 | | |

TABLE II

Fungicidal Activity

| | | Mycelial Inhibition | | | | | | | | | | | |
|---|---|---|---|---|---|---|---|---|---|---|---|---|---|
| Compound No. | | Pyth. | Rhiz. | Fusar. | Botry. | Asper. | Ustil. | GDM | TLB | RB | TEB | CLB | BPM | BR |
| 1 | 42642 | 0 | 0 | 0 | 0 | 0 | — | 21 | 0 | 0 | 13 | 7 | 0 | 7 |
| 2 | 42533 | 21 | 38 | 57 | 93 | 133 | — | 97 | 97 | 70 | — | 92 | 58 | 0 |
| 3 | 43531 | 0 | 0 | 0 | 0 | 0 | 35 | — | 87 | 72 | 33 | 75 | 100 | 0 |
| 4 | 45266 | 38 | 57 | 86 | 50 | 179 | 48 | — | 81 | 88 | — | 95 | 75 | 0 |
| 5 | 45129 | 47 | 40 | 136 | 44 | 107 | 43 | — | 99 | 60 | — | 92 | 0 | 0 |
| 6 | 45058 | 0 | 31 | 68 | 0 | 130 | 36 | — | 98 | 25 | 35 | 99 | 100 | 0 |
| 7 | 44876 | 0 | 0 | 45 | 19 | 67 | 25 | — | 94 | 0 | 33 | 86 | 100 | 0 |
| 8 | 44104 | 0 | 20 | 94 | 0 | 79 | 70 | — | 94 | — | 0 | 90 | 100 | 0 |
| 9 | 44570 | 20 | 50 | 80 | 25 | 210 | 35 | — | 100 | 86 | 0 | 100 | 0 | 0 |
| 10 | 45265 | 0 | 0 | 86 | 0 | 0 | 53 | — | 50 | 25 | 0 | 98 | 88 | 0 |
| 11 | 45359 | 0 | 0 | 68 | 0 | 83 | 24 | — | 19 | — | 0 | 94 | 100 | 0 |
| 12 | 43777 | 0 | — | 38 | 25 | 0 | 0 | — | 94 | 0 | 0 | 99 | 100 | 0 |
| 13 | 44828 | 0 | 0 | 0 | 0 | 0 | 0 | — | 0 | 0 | 0 | 0 | 0 | 0 |
| 14 | 43778 | 0 | — | 0 | 0 | 0 | 43 | — | 94 | 0 | 8 | 90 | 100 | 0 |
| 15 | 45287 | 31 | 100 | 128 | 38 | 100 | 75 | — | 63 | 40 | — | 100 | 0 | 0 |
| 16 | 45361 | 0 | 0 | 84 | 0 | 133 | 60 | — | 0 | — | 35 | 100 | 100 | 0 |

Pyth. = *Pythium ultimum*
Rhiz. = *Rhizoctonia solani*
Fusar. = *Fusarium moniloforme*
Botry. = *Botrytis cinerea*
Asper. = *Aspergillus niger*
Ustil. = *Ustilago hordeii*
— = Test Failed
GDM = Grape Downy Mildew
TLB = Tomato Late Blight
RB = Rice Blast
TEB = Tomato Early Blight
CLB = Celery Late Blight
BPM = Bean Powdery Mildew
BR = Bean Rust

TABLE III

Insecticidal Activity

| Compound No. | | AR | AW | HF | MA | ME | Aph | AS | CL | 5-CL |
|---|---|---|---|---|---|---|---|---|---|---|
| 1 | 42642 | 60 | — | 100 | 90 | 0 | 80 | — | 80 | 100 |
| 2 | 42533 | 60 | — | 30 | 80 | 100 | 30 | 0 | 80 | 90 |
| 3 | 43531 | 0 | 0 | 0 | 80 | 40 | 20 | 0 | 80 | 20 |
| 4 | 45266 | 30 | — | 60 | 100 | 100 | 50 | 0 | 100 | 100 |
| 5 | 45129 | 90 | — | 40 | 100 | 80 | 80 | 0 | 40 | 80 |
| 6 | 45058 | 0 | — | 75 | 95 | 50 | 0 | 0 | 10 | 80 |
| 7 | 44876 | 0 | 0 | 0 | 40 | 0 | 0 | 0 | 30 | 100 |
| 8 | 44104 | 0 | 0 | 0 | 80 | 100 | 0 | 0 | 0 | 0 |
| 9 | 44570 | 50 | 0 | 30 | 95 | 100 | 80 | 0 | 100 | 100 |
| 10 | 45265 | 0 | — | 0 | 90 | 50 | 0 | 0 | 0 | 50 |
| 11 | 45359 | 0 | — | 40 | 90 | 80 | 0 | 0 | 0 | 0 |
| 12 | 43777 | 0 | 0 | 0 | 95 | 100 | 0 | 0 | 10 | 70 |
| 13 | 44828 | 0 | — | 0 | 0 | 0 | 0 | 0 | 0 | 90 |
| 14 | 43778 | 0 | 0 | 0 | 90 | 70 | 0 | 0 | 10 | 90 |
| 15 | 45287 | 50 | — | 100 | 100 | 100 | 30 | 0 | 100 | 100 |
| 16 | 45361 | 0 | — | 40 | 20 | 0 | 0 | 0 | 0 | 50 |

AR = American Cockroach
AW = Alfalfa Weevil
HF = Housefly
MA = Mite Adult
ME = Mite Egg
Aph. = Aphid
AS = Aphid Systemic
CL = Cabbage Looper
5-CL = 5-Day Reading of Cabbage Looper Mortality

TABLE IV

HERBICIDAL ACTIVITY

| | | Pre-Emergent | | | | | | | | Post-Emergent | | | | | | | |
|---|---|---|---|---|---|---|---|---|---|---|---|---|---|---|---|---|---|
| Compound No. | | LQ | Mus | Pgw | BG | CG | WO | SB | R | LQ | Mus | Pgw | BG | CG | WO | SB | R |
| 1 | 42642 | 100 | 100 | 100 | 92 | 98 | 95 | 80 | 92 | 100 | 100 | 30 | 0 | 0 | 0 | 40 | 0 |
| 2 | 42533 | 0 | 0 | 0 | 0 | 0 | 0 | 0 | 0 | 55 | 100 | 50 | 40 | 25 | 35 | 60 | 25 |
| 3 | 43531 | 0 | 0 | 0 | 0 | 0 | 0 | 0 | 0 | 0 | 0 | 0 | 0 | 0 | 0 | 0 | 0 |
| 4 | 45266 | 60 | 40 | 30 | 45 | 60 | 15 | 15 | 0 | 35 | 100 | 85 | 85 | 40 | 60 | 55 | 30 |
| 5 | 45129 | 0 | 0 | 20 | 30 | 50 | 0 | 25 | 0 | 20 | 100 | 95 | 55 | 10 | 30 | 65 | 15 |
| 6 | 45058 | 0 | 0 | 30 | 25 | 0 | 0 | 25 | 0 | 0 | 0 | 0 | 0 | 0 | 0 | 0 | 0 |
| 7 | 44876 | 0 | 0 | 0 | 0 | 0 | 0 | 0 | 0 | 0 | 0 | 0 | 0 | 0 | 0 | 0 | 0 |
| 8 | 44104 | 0 | 0 | 0 | 0 | 0 | 0 | 0 | 0 | 10 | 40 | 25 | 0 | 0 | 0 | 0 | 0 |
| 9 | 44570 | 0 | 0 | 0 | 0 | 25 | 0 | 0 | 0 | 98 | 100 | 97 | 40 | 40 | 40 | 65 | 25 |
| 10 | 45265 | 0 | 0 | 0 | 0 | 0 | 0 | 0 | 0 | 0 | 15 | 10 | 0 | 0 | 0 | 0 | 0 |
| 11 | 45359 | 0 | 0 | 0 | 0 | 0 | 0 | 0 | 0 | 0 | 0 | 0 | 0 | 0 | 0 | 0 | 0 |

TABLE IV-continued

| | HERBICIDAL ACTIVITY | | | | | | | | | | | | | | | |
|---|---|---|---|---|---|---|---|---|---|---|---|---|---|---|---|---|
| | Pre-Emergent | | | | | | | | Post-Emergent | | | | | | | |
| Compound No. | LQ | Mus | Pgw | BG | CG | WO | SB | R | LQ | Mus | Pgw | BG | CG | WO | SB | R |
| 12 43777 | 0 | 0 | 0 | 0 | 0 | 0 | 0 | 0 | 0 | 0 | 0 | 15 | 10 | 10 | 0 | 10 |
| 13 44828 | 0 | 0 | 0 | 0 | 0 | 0 | 0 | 0 | 0 | 0 | 0 | 0 | 0 | 0 | 0 | 0 |
| 14 43778 | 0 | 0 | 0 | 0 | 0 | 0 | 0 | 0 | 0 | 0 | 0 | 0 | 0 | 0 | 0 | 0 |
| 15 45287 | 0 | 0 | 0 | 0 | 0 | 0 | 0 | 0 | 35 | 85 | 85 | 30 | 25 | 20 | 65 | 20 |
| 16 45361 | 0 | 0 | 0 | 0 | 0 | 0 | 15 | 0 | 0 | 0 | 0 | 0 | 0 | 0 | 0 | 0 |

What is claimed is:

1. A compound of the formula:

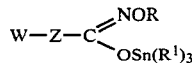

wherein W is aryl of 6 to 12 carbon atoms, substituted aryl of 6 to 12 carbon atoms substituted with 1 to 3 substituents independently selected from halogen, nitro, lower alkoxy of 1 to 3 carbon atoms, lower alkylthio of 1 to 3 carbon atoms or lower alkyl of 1 to 3 carbon atoms; lower cycloalkyl of 3 to 7 carbon atoms; or substituted lower cycloalkyl of 3 to 7 carbon atoms substituted with 1 to 3 lower alkyl groups; Z is a direct link, lower alkylene of 1 to 6 carbon atoms, or lower alkenylene of 2 to 6 carbon atoms; R is lower alkyl of 1 to 6 carbon atoms or benzyl; and $R^1$ is phenyl, lower alkyl of 1 to 6 carbon atoms, or lower cycloalkyl of 3 to 8 carbon atoms, either optionally substituted with 1 to 3 independently selected halogen atoms.

2. A compound according to claim 1 wherein Z is a direct link.

3. A compound according to claim 2 wherein W is phenyl or phenyl substituted with nitro, halogen, lower alkyl, lower alkoxy or lower alkylthio.

4. A compound according to claim 3 wherein W is phenyl, 2-nitrophenyl, 2-fluorophenyl, or 2,4-dinitrophenyl.

5. A compound according to claim 4 wherein $R_1$ is cyclohexyl.

6. A compound according to claim 2 wherein W is lower cycloalkyl or substituted lower cycloalkyl.

7. A compound according to claim 6 wherein W is 1-methylcycloalkyl.

8. A compound according to claim 7 wherein W is 1-methylcyclopropyl.

9. A compound according to claim 8 wherein $R_1$ is cyclohexyl.

10. A compound according to claim 1 wherein Z is lower alkenylene.

11. A compound according to claim 10 wherein Z is vinylene.

12. A compound according to claim 11 wherein W is aryl or substituted aryl.

13. A compound according to claim 12 wherein W is 4-tolyl.

14. A compound according to claim 13 wherein $R^1$ is cyclohexyl.

15. A compound according to claim 14 wherein R is methyl.

16. A compound according to claim 1 wherein Z is lower alkylene.

17. A compound according to claim 1 wherein $R^1$ is cyclohexyl.

18. A method of controlling fungi which comprises contacting said fungi or their growth environment with a fungicidally effective amount of a compound of claim 1.

19. A method of controlling fungi which comprises contacting said fungi or their growth environment with a fungicidally effective amount of a compound of claim 2.

20. A method of controlling fungi which comprises contacting said fungi or their growth environment with a fungicidally effective amount of a compound of claim 6.

21. A method of controlling fungi which comprises contacting said fungi or their growth environment with a fungicidally effective amount of a compound of claim 10.

22. A method of controlling fungi which comprises contacting said fungi or their growth environment with a fungicidally effective amount of a compound of claim 15.

23. A method of controlling fungi which comprises contacting said fungi or their growth environment with a fungicidally effective amount of a compound of claim 16.

24. A fungicidal composition which comprises an inert carrier and a fungicidally effective amount of a compound of claim 1.

25. A fungicidal composition which comprises an inert carrier and a fungicidally effective amount of a compound of claim 2.

26. A fungicidal composition which comprises an inert carrier and a fungicidally effective amount of a compound of claim 6.

27. A fungicidal composition which comprises an inert carrier and a fungicidally effective amount of a compound of claim 10.

28. A fungicidal composition which comprises an inert carrier and a fungicidally effective amount of a compound of claim 15.

29. A fungicidal composition which comprises an inert carrier and a fungicidally effective amount of a compound of claim 16.

* * * * *